(12) United States Patent
Mae et al.

(10) Patent No.: US 6,184,255 B1
(45) Date of Patent: Feb. 6, 2001

(54) PHARMACEUTICAL COMPOSITION COMPRISING COENZYME $Q_{10}$

(75) Inventors: Tatsumasa Mae, Kakogawa; Yoshitomo Sakamoto, Akashi; Souichi Morikawa, Himeji; Takayoshi Hidaka, Kobe, all of (JP)

(73) Assignee: Kaneka Corporation, Osaka (JP)

( * ) Notice: Under 35 U.S.C. 154(b), the term of this patent shall be extended for 0 days.

(21) Appl. No.: 09/242,327

(22) PCT Filed: Aug. 18, 1997

(86) PCT No.: PCT/JP97/02845

§ 371 Date: May 26, 1999

§ 102(e) Date: May 26, 1999

(87) PCT Pub. No.: WO98/07417

PCT Pub. Date: Feb. 26, 1998

(30) Foreign Application Priority Data

Aug. 16, 1996 (JP) .................................................. 8-234729
Jun. 13, 1997 (JP) .................................................. 9-173191

(51) Int. Cl.[7] .......................... A61K 31/075; A01N 31/14
(52) U.S. Cl. .......................... 514/720; 514/720; 514/824; 514/878; 514/879
(58) Field of Search .................................... 514/720, 824, 514/878, 879

(56) References Cited

U.S. PATENT DOCUMENTS 3,349,113 * 10/1967 Gloor et al. .......................... 260/476
5,312,819 * 5/1994 Fischer et al. ........................ 514/220
5,648,377 * 7/1997 Bombardelli et al. ................ 514/456

FOREIGN PATENT DOCUMENTS

| 198839B | 2/1989 | (HU) . |
| 1190442 * | 11/1985 | (IT) . |
| 59-47202A | 3/1984 | (JP) . |
| 59-47202 * | 3/1984 | (JP) . |
| 4-89456 * | 3/1992 | (JP) . |
| 4-89456A | 3/1992 | (JP) . |

OTHER PUBLICATIONS

"Effect of Dietary Coenzyme Q as an Antioxidant in Human Plasma", Molec. Aspects. Med., vol. 15 (Supplement), pp. s97–s102, Dec. 1994.*

Weber, C. et al., Molec. Aspects Med., (1994) vol. 15 (Supplement), pp. S97–S102.

* cited by examiner

Primary Examiner—Frederick Krass
(74) Attorney, Agent, or Firm—Pollock, Vande Sande & Amernick

(57) ABSTRACT

The present invention has for its object to provide a medicinal composition comprising coenzyme $Q_{10}$ as an active ingredient, which composition features an enhanced absorption after oral administration. The present invention is directed to a medicinal composition comprising coenzyme $Q_{10}$ as an active ingredient with the reduced form of coenzyme $Q_{10}$ accounting for more than 20 weight % of said coenzyme $Q_{10}$.

7 Claims, 2 Drawing Sheets

PHARMACEUTICAL COMPOSITION COMPRISING COENZYME $Q_{10}$

This application is a 317 of PCT/JP97/02845, filed Aug. 18, 1997.

TECHNICAL FIELD

The present invention relates to a medicinal composition with improved absorption after oral administration which comprises a coenzyme $Q_{10}$ of the following general formula (1-A) as an active ingredient.

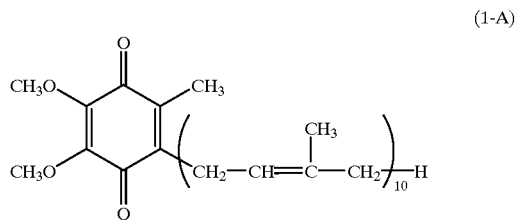

BACKGROUND ART

Coenzyme $Q_{10}$ is a class of physiological substances occurring as component factors of the mitochondrial electron transfer system within the biological cell. Coenzyme $Q_{10}$ acts directly as an electron carrier in the oxidative phosphorylation reactions, through metabolic pathways, particularly aerobic pathways, to produce ATP and hence energy.

It seems that the demand for coenzyme $Q_{10}$ is increased in normal subjects in the state of severe physical fatigue and patients with cardiovascular disease, chronic debilitating disease, or on prolonged pharmacotherapy. It has been shown that a deficiency of coenzyme $Q_{10}$ occurs particularly in ischemic heart diseases, senile myocardial sclerosis, and hypertensive heart diseases. Therefore, it is a sound therapeutic choice to administer coenzyme $Q_{10}$ to those patients.

Moreover, coenzyme $Q_{10}$ has been used for non-therapeutic purposes as a nutrient or nutritional supplement just like vitamins.

In order that coenzyme $Q_{10}$ may express its therapeutic efficacy or nutritional effect, it is most important to increase the coenzyme $Q_{10}$ level within the patient's tissue cells.

Coenzyme $Q_{10}$ is a lipid-soluble and practically water-insoluble substance and, therefore, it is only sparingly soluble in gastric juice. Consequently, oral dosage forms containing coenzyme $Q_{Q10}$ in solid state, such as tablets, granules, capsules, and suspensions for extemporaneous preparation, are not well absorbed after oral administration. This means that a considerably greater amount of coenzyme $Q_{10}$ than actually needed must be administered to the patient but such a practice tends to cause adverse gastrointestinal reactions such as epigastric discomfort, anorexia, nausea, and diarrheas.

Much research has heretofore been undertaken for overcoming those disadvantages. Japanese Kokai Publications Sho-55-81813 and Sho-61-221131, among others, disclose coenzyme $Q_{10}$ formulations of the solution type or the emulsion/dispersion type. However, such pharmaceutical devices are not sufficient to improve the absorption of coenzyme $Q_{10}$ in a satisfactory measure.

Japanese Kokai Publication Sho-56-18914 discloses a technology for accelerating the lymphatic absorption of coenzyme $Q_{10}$. This technology has been demonstrated to increase the absorption of coenzyme $Q_{10}$ in a certain measure but has not proved practically useful as yet.

Japanese Kokai Publication Sho-60-89442 discloses a cyclodextrin-clathrated coenzyme $Q_{10}$ formulation. Japanese Kokai Publication Sho-60-1124 discloses a coenzyme $Q_{10}$-containing ribosomal formulation. However, those coenzyme $Q_{10}$ preparations require a complicated pharmaceutical procedure for production and are not practically fully satisfactory.

Italian Patent 1190442 Specification discloses a technology which, instead of using coenzyme $Q_{10}$ as such, comprises converting a reduced form of coenzyme $Q_{10}$ to a derivative such as an acyl ester, a sulfuric acid ester, or a phosphoric acid ester and administering this coenzyme $Q_{10}$ derivative for enhanced absorption. However, the effect of the technology has not been supported by experimental data.

SUMMARY OF THE INVENTION

The present invention has for its object to provide a medicinal composition comprising coenzyme $Q_{10}$ as an active ingredient, which composition features an enhanced absorption after oral administration.

In the course of their intensive research for overcoming the above-mentioned disadvantages of the prior art, the inventors of the present invention discovered that when a medicinal composition containing a reduced form of coenzyme $Q_{10}$ was prepared and administered to patients by the oral route, a considerably higher bioavailability was surprisingly obtained as compared with the conventional medicinal composition containing only the oxidized form of coenzyme $Q_{10}$. The present invention has been developed on the basis of the above finding.

The present invention, therefore, is directed to a medicinal composition comprising coenzyme $Q_{10}$ as an active ingredient with the reduced form of coenzyme $Q_{10}$ accounting for more than 20 weight % of said coenzyme $Q_{10}$.

DETAILED DESCRIPTION OF THE INVENTION

Figure 1:
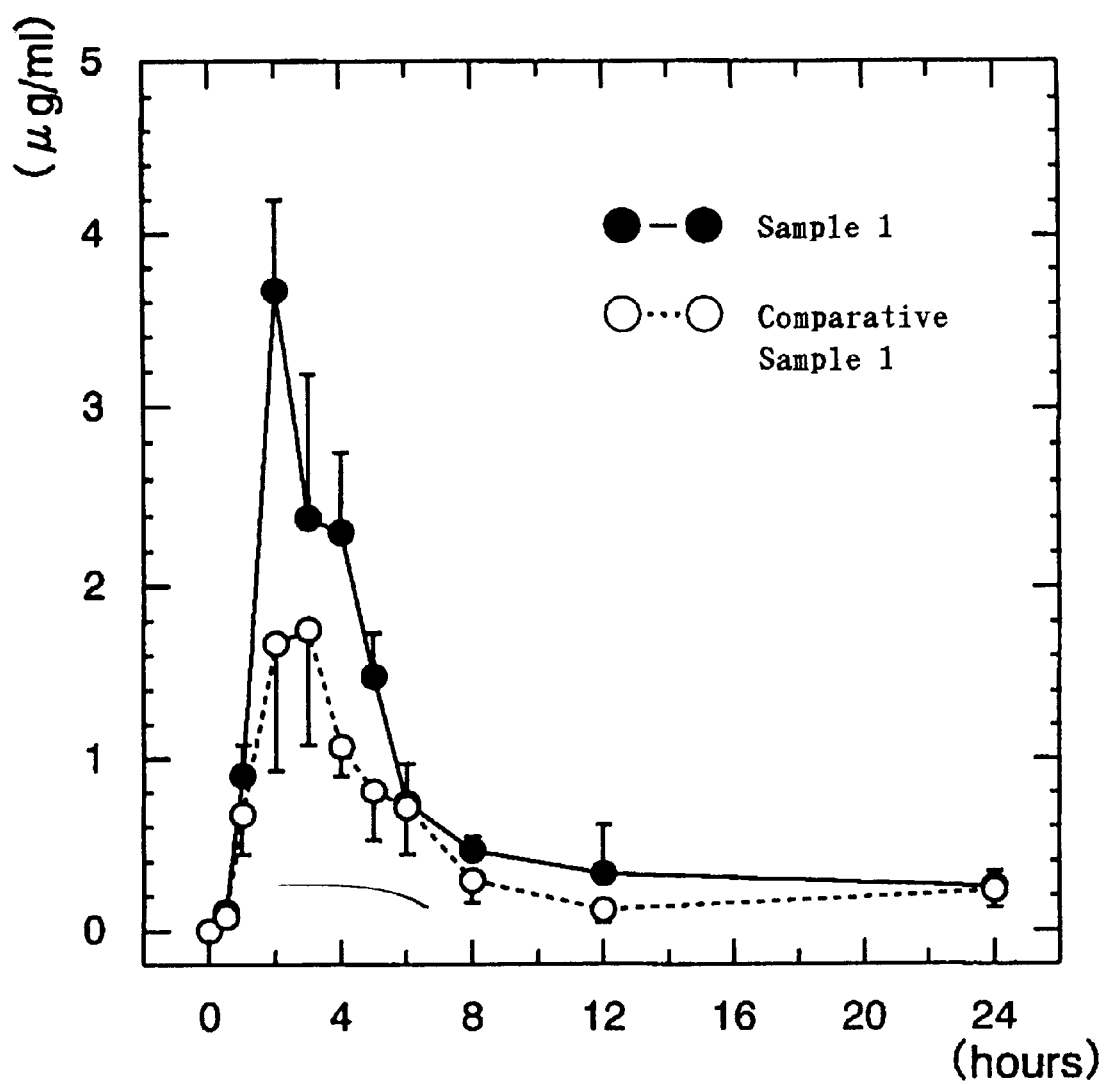
FIG. 1 is a graphical representation of the relationship of plasma total coenzyme $Q_{10}$ concentration with the time after administration. The ordinate represents the plasma total coenzyme $Q_{10}$ concentration and the abscissa represents the time after administration. Each plot represents mean±standard deviation (n=4).

The present invention is now described in detail.

It is known that a fairly high proportion, usually about 40 to 90%, of coenzyme $Q_{10}$ occurs in reduced form in the body. In vivo, the reduced form of coenzyme $Q_{10}$ is readily transformed to the oxidized form, while the oxidized form of coenzyme $Q_{10}$ is readily transformed into the reduced form. Therefore, coenzyme $Q_{10}$ in vivo can be generally expressed by the following formula (1).

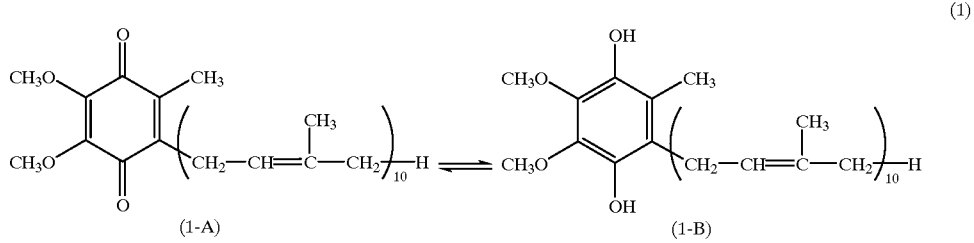

Referring to the above formula (1), the general formula (1-A) represents the oxidized form of coenzyme $Q_{10}$ and the general formula (1-B) represents the reduced form of coenzyme $Q_{10}$.

In the conventional medicinal composition containing a coenzyme $Q_{10}$ as an active ingredient, the sole active ingredient is the oxidized form of coenzyme $Q_{10}$ of the above chemical formula (1-A). In contrast, the medicinal composition of the present invention comprises a reduced form of coenzyme $Q_{10}$ of the above chemical formula (1-B) as an active ingredient coenzyme $Q_{10}$. Consequently, as compared with the conventional medicinal composition containing only the oxidized form of coenzyme $Q_{10}$ as an active ingredient, the medicinal composition of the present invention is improved in absorption after oral administration and insures a higher bioavailability.

There is no particular limitation on the technology for providing said reduced form of coenzyme $Q_{10}$. A typical method, which is by no means exclusive, comprises harvesting a coenzyme $Q_{10}$ from a synthetic reaction mixture, a fermentation broth, or a natural source by procedures known in the art and subjecting it to chromatography to separate and concentrate the reduced form of coenzyme $Q_{10}$ fraction. Where necessary, there can be followed the procedure of adding a conventional reducing agent such as sodium borohydride or sodium dithionite (sodium hydrosulfite) to the above coenzyme $Q_{10}$ to reduce the oxidized form of coenzyme $Q_{10}$ fraction of said coenzyme $Q_{10}$ and, then, concentrate the reduced $Q_{10}$ by chromatography. As a further alternative, the objective reduced form of coenzyme $Q_{10}$ can be obtained by permitting said reducing agent to act on the available high-purity coenzyme $Q_{10}$.

There is no particular limitation on the technology for manufacturing the medicinal composition of the present invention. A typical but by no means exclusive method comprises dissolving the reduced form of coenzyme $Q_{10}$ thus obtained and a commercial oxidized form of coenzyme $Q_{10}$ in a suitable common solvent such as isopropyl alcohol, acetone, or ether to provide a medicinal composition containing said reduced form of coenzyme $Q_{10}$ in a desired proportion. As an alternative, the above-mentioned reduced and oxidized forms of coenzyme $Q_{10}$ can be simply admixed in solid stage. It is also possible to directly use the mixture of oxidized and reduced forms of coenzyme $Q_{10}$ obtained in the course of the above-mentioned production process for coenzyme $Q_{10}$. Furthermore, the active ingredient for the medicinal composition of the present invention can be directly obtained by controlling the time of reduction reaction of the high-purity coenzyme $Q_{10}$ already available and the type or amount of reducing agent to be used.

In the medicinal composition of the present invention, the reduced form of coenzyme $Q_{10}$ accounts for more than 20 weight % of the total amount of coenzyme $Q_{10}$. If its proportion is not less than 20 weight %, the bioavailability of the resulting medicinal composition will not be as high as expected. The preferred proportion is not less than 40 weight % and the most preferred proportion is not less than 60 weight %. Conversely if the proportion of the reduced form of coenzyme $Q_{10}$ is too large, the production process will be complicated and the cost of production increased. Therefore, it is not necessary to increase the coenzyme $Q_{10}$ content too much.

The medicinal composition of the present invention can be used as, for example, a cardiotonic effective against symptoms in ischemic heart disease, senile myocardial sclerosis, hypertensive heart disease, etc. It can also be used as a nutrient, a nutritional supplement, or a veterinary medicine.

There is no particular limitation on the dosage form for the medicinal composition of the present invention. It may for example be powders, granules containing a binder component, or compression-molded tablets. Such powders or granules may be filled in capsule shells to provide capsules. They may also be processed into soft capsules by adding a natural oil, an oily higher fatty acid, a higher fatty acid monoglyceride, or a mixture thereof and wrapping the medicated oil in soft capsule sheet materials. In this application, the capsule shell may be one predominantly composed of gelatin or any other water-soluble macromolecular substance. The capsule includes microcapsules.

The medicinal composition of the present invention may contain, in addition to said reduced form of coenzyme $Q_{10}$, a variety of pharmaceutically acceptable formulating substances as added in suitable amounts in the routine manner. There is no particular limitation on the kinds of such substances. Thus, an excipient, a disintegrator, a lubricant, a binder, an antioxidant, a coloring agent, an antiflocculant, an absorption promoter, a solubilizer for the active ingredient, a stabilizer, etc. can be added as necessary.

The above-mentioned excipient includes but is not limited to sucrose, lactose, glucose, corn starch, mannitol, crystalline cellulose, calcium phosphate, and calcium sulfate.

The disintegrator includes but is not limited to starch, agar, calcium citrate, calcium carbonate, sodium hydrogen carbonate, dextrin, crystalline cellulose, carboxymethylcellulose, and gum tragacanth.

The lubricant includes but is not limited to talc, magnesium stearate, polyethylene glycol, silica, and hydrogenated vegetable oil.

The binder includes but is not limited to ethylcellulose, methylcellulose, hydroxypropylmethylcellulose, gum tragacanth, shellac, gelatin, gum arabic, polyvinylpyrrolidone, polyvinyl alcohol, polyacrylic acid, polymethacrylic acid, and sorbitol.

The antioxidant includes but is not limited to ascorbic acid, tocopherol, vitamin A, β-carotene, sodium hydrosulfite, sodium thiosulfate, sodium pyrolsulfite, and citric acid.

There is no particular limitation on the coloring agent that can be used. For example, a variety of pharmaceutically acceptable colors can be mentioned.

The antiflocculant includes but is not limited to stearic acid, talc, light silicic anhydride, and hydrous silicon dioxide.

The absorption promoter includes but is not limited to higher alcohols, higher fatty acids, and glycerin fatty acid esters and other surfactants.

The above-mentioned solubilizer for the active ingredient includes but is not limited to organic acids such as fumaric acid, succinic acid, and malic acid.

The stabilizer includes but is not limited to benzoic acid, sodium benzoate, and ethyl p-hydroxybenzoate.

When the preparation comprising the medicinal composition of the present invention is used for by oral administration, the dosage should be selected according to the usage such as a drug, a veterinary medicine, or a nutrient.

For oral administration to domestic animals or fowls, the composition can be used as admixed into the feed or administered by a conventional forced manner.

BEST MODE FOR CARRYING OUT THE INVENTION

The following examples and formulation examples are intended to illustrate the present invention in further detail and should by no means be limitative of the scope of the present invention.

EXAMPLE 1

(1) Preparation of Samples
Preparation of Sample 1

A 5:95 (w/w) mixture (0.3 g) of oxidized form of coenzyme $Q_{10}$ and reduced form of coenzyme $Q_{10}$ was melted on a water bath at 50° C. and an olive oil was added to the melt to make 6.0 ml. This mixture was homogenized at 50° C. to provide an oily composition.

Preparation of Comparative Sample 1

Oxidized coenzyme $Q_{10}$ (0.3 g) was melted on a water bath at 50° C. and an olive oil was added to the melt to make 6.0 ml. This mixture was homogenized at 50° C. to provide an oily composition.

(2) Oral Absorption Test

Sample 1 and Comparative Sample 1 were used as test samples. The test was performed using male Crj:CD (SD) rats (body weights 260 to 300 g) under well-fed conditions. As to dosage, each test sample was administered orally at the rate of 100 mg of total coenzyme $Q_{10}$ per kg body weight. In the test, the total plasma coenzyme $Q_{10}$ concentration was determined before administration (not administered) and serially after administration. Four rats were used per test sample for each time-point. The total coenzyme $Q_{10}$ means the sum of the mixture comprising the oxidized and reduced forms of coenzyme $Q_{10}$. The total plasma coenzyme $Q_{10}$ concentration was assayed as the concentration of oxidized form of coenzyme $Q_{10}$ in the following manner. To 1.0 ml of the obtained plasma sample, 2.0 ml of water, 4.0 ml of ethanol, and 10.0 ml of n-hexane were added in the order mentioned. The mixture was shaken vigorously for about 5 minutes and then centrifuged to separate into two layers. The organic layer was taken and the aqueous layer was further extracted with 10.0 ml of n-hexane twice in the same manner. The resulting organic layers and the organic layer previously taken were combined and evaporated to dryness. To the residue was added 250 μl of ethanol:1N-hydrochloric acid (99:1, v/v) for use as an assay sample. The assay of coenzyme $Q_{10}$ was carried out by high-performance liquid chromatography under the following conditions.

Column: 250 mm long×4.6 mm in diameter SYMMETRY C18 (Waters)
Mobile phase: 0.5 M $NaClO_4$/$C_2H_5OH:CH_3OH:CH_3CN:70\%HClO_4$(400:300:300:1, v:v)
Detection wavelength: 275 nm
Flow rate: 1 ml/min.

The test results are presented in FIG. 1. In FIG. 1, the ordinate represents total plasma coenzyme $Q_{10}$ concentration and the abscissa represents the time after administration. Each plot is mean±standard deviation.

It is apparent from FIG. 1 that whereas the plasma concentration peak appeared at 3 hr after administration in the case of the composition containing only the oxidized form of coenzyme $Q_{10}$, the peak appeared 1 hour earlier, i.e. at 2 hours after administration, in the case of the composition comprising the reduced form of coenzyme $Q_{10}$. Furthermore, the concentration level is also 2.1 times as high for the composition comprising the reduced form of coenzyme $Q_{10}$. It is, thus, clear that compared with the composition containing only the oxidized form of coenzyme $Q_{10}$, the medicinal composition of the present invention is absorbed faster and in a larger amount.

EXAMPLE 2

(1) Preparation of Samples
Preparation of Sample 2

Using a 20:80 (w/w) mixture of oxidized form of coenzyme $Q_{10}$ and reduced form of coenzyme $Q_{10}$, Test Sample 2 was prepared in the same manner as the preparation of Sample 1 in Example 1.

Preparation of Sample 3

Using a 40:60 (w/w) mixture of oxidized form of coenzyme $Q_{10}$ and reduced form of coenzyme $Q_{10}$, Test Sample 3 was prepared in the same manner as the preparation of Sample 1 in Example 1.

Preparation of Sample 4

Using a 60:40 (w/w) mixture of oxidized form of coenzyme $Q_{10}$ and reduced form of coenzyme $Q_{10}$, Test Sample 4 was prepared in the same manner as the preparation of Sample 1 in Example 1.

Preparation of Comparative Sample 2

Using a 80:20 (w/w) mixture of oxidized form of coenzyme $Q_{10}$ and reduced form of coenzyme $Q_{10}$, Comparative Sample 2 was prepared in the same manner as the preparation of Sample 1 in Example 1.

(2) Oral Absorption Test

Sample 1, Sample 2, Sample 3, Sample 4, Comparative Sample 1, and Comparative Sample 2 were used as test samples.

The test was performed in the same manner as described in Example 1 except that the determination of total plasma coenzyme $Q_{10}$ concentration was carried out at 3 hours after administration.

Figure 2:
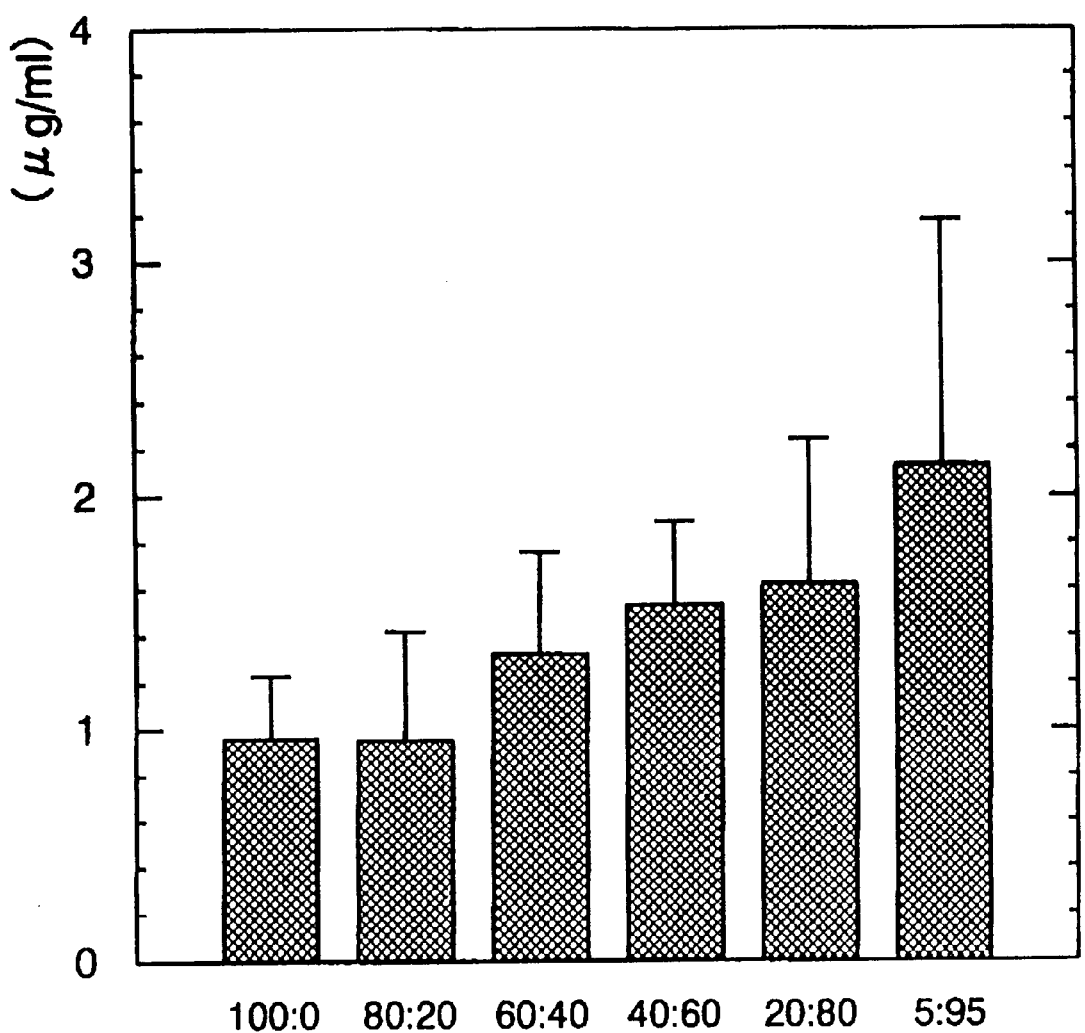
FIG. 2 is a graphical representation of the relationship of the total plasma coenzyme $Q_{10}$ concentration at 3 hours after administration with the weight ratio of oxidized form of coenzyme $Q_{10}$ to reduced form of coenzyme $Q_{10}$ in each sample. The ordinate represents the plasma total coenzyme $Q_{10}$ concentration and the abscissa represents the oxidized form of coenzyme $Q_{10}$-reduced form of coenzyme $Q_{10}$ ratio by weight. Each bar represents mean±standard deviation (n=4).

The test results are presented in FIG. 2. In FIG. 2, the ordinate represents the total plasma coenzyme $Q_{10}$ concentration at 3 hours after administration and the abscissa represents the weight ratio of oxidized form of coenzyme $Q_{10}$ to reduced form of coenzyme $Q_{10}$ in the test sample. Each bar represents mean±standard deviation.

It is apparent from FIG. 2 that compared with the composition containing only the oxidized form of coenzyme $Q_{10}$ and the composition in which the reduced form of coenzyme $Q_{10}$ accounts for 20 weight % of total coenzyme $Q_{10}$, administration of the compositions in which reduced form of coenzyme $Q_{10}$ accounts for 40 weight % or more of total coenzyme $Q_{10}$ resulted in higher plasma coenzyme $Q_{10}$ concentrations. Moreover, with a weight ratio of contained reduced form of coenzyme $Q_{10}$ increasing, the plasma coenzyme $Q_{10}$ concentration was further increased. Those results indicate that because it contains 40 weight % or more of the reduced form of coenzyme $Q_{10}$, the medicinal composition of the present invention is absorbed in a definitely larger amount than the composition containing only the oxidized form of coenzyme $Q_{10}$ and the composition in which the reduced form of coenzyme $Q_{10}$ accounts for 20 weight % or less of the total coenzyme $Q_{10}$ content.

Then, using a 15:85 (w/w) mixture of oxidized form of coenzyme $Q_{10}$ and reduced form of coenzyme $Q_{10}$ (hereinafter referred to as main medicine) as an active ingredient, several dosage forms were prepared by the conventional pharmaceutical procedures.

Formulation Example 1 (Powders)

The main medicine was dissolved in acetone and the solution was adsorbed on microcrystalline cellulose, followed by drying. The product was mixed with corn starch to provide powders in the routine manner.

| Main medicine | 10 Parts by weight |
|---|---|
| Microcrystalline cellulose | 40 Parts by weight |
| Corn starch | 55 Parts by weight |

Formulation Example 2 (Tablets)

The main medicine was dissolved in acetone and the solution was adsorbed on microcrystalline cellulose, followed by drying. The product was mixed with corn starch, lactose, carboxymethylcellulose, and magnesium stearate and the mixture was granulated in the routine manner by adding an aqueous solution of polyvinylpyrrolidone as a binder. To the granules thus obtained was added talc as a lubricant followed by mixing and the resulting composition was compressed into tablets each containing 20 mg of the main medicine.

| Main medicine | 20 Parts by weight |
|---|---|
| Corn starch | 25 Parts by weight |
| Lactose | 15 Parts by weight |
| Carboxymethylcellulose calcium | 10 Parts by weight |
| Microcrystalline cellulose | 40 Parts by weight |
| Polyvinylpyrrolidone | 5 Parts by weight |
| Magnesium stearate | 3 Parts by weight |
| Talc | 10 Parts by weight |

Formulation Example 3 (Capsules)

The following components were granulated by the routine procedure and filled in hard gelatin capsule shells to provide capsules each containing 20 mg of the main medicine.

| Main medicine | 20 Parts by weight |
|---|---|
| Microcrystalline cellulose | 40 Parts by weight |
| Corn starch | 20 Parts by weight |
| Lactose | 62 Parts by weight |
| Magnesium stearate | 2 Parts by weight |
| Polyvinylpyrrolidone | 3 Parts by weight |

Formulation Example 4 (Soft Capsules)

Soybean oil was warmed to 60° C. and the main medicine melted at 60° C. was added and dissolved. Then, vitamin E was added gradually to prepare a homogeneous mixture, which was then processed into soft capsules each containing 20 mg of the main medicine.

| Main medicine | 20 Parts by weight |
|---|---|
| Vitamin E | 15 Parts by weight |
| Soybean oil | 350 Parts by weight |

INDUSTRIAL AVAILABILITY

Because of the above constitution, the medicinal composition of the present invention is well absorbable after oral administration and shows a high level of bioavailability.

What is claimed is:

1. A medicinal composition comprising coenzyme $Q_{10}$ as an active ingredient with the reduced form of coenzyme $Q_{10}$ accounting for more than 20 weight % and not more than 95 weight % of said coenzyme $Q_{10}$.

2. The medicinal composition according to claim 1 wherein said reduced form of coenzyme $Q_{10}$ accounts for 40 weight % or more of the total coenzyme $Q_{10}$ content.

3. The medicinal composition according to claim 1 wherein the reduced form of coenzyme $Q_{10}$ accounts for 60 weight % or more of the total $Q_{10}$ content.

4. The medicinal composition of claim 1 which further contains at least one member selected from the group consisting of excipient, disintegrator, lubricant, binder, antioxidant, coloring agent, antiflocculant, absorption promoter, solubilizer, and stabilizer.

5. A method for treating a patient suffering from a deficiency of coenzyme $Q_{10}$ which comprises orally administering to the patient an effective amount of the medicinal composition of claim 1.

6. A method for improving absorption after oral administration of a medicinal composition of coenzyme $Q_{10}$ which comprises orally administering to a patient an effective amount of coenzyme $Q_{10}$ as an active ingredient with the reduced form of coenzyme $Q_{10}$ accounting for more than 20 weight % and not more than 95 weight % of the total coenzyme $Q_{10}$ content.

7. The method according to claim 6 wherein said reduced form of coenzyme $Q_{10}$ accounts for more than 40 weight % of the total coenzyme $Q_{10}$ content.

* * * * *